US00PP34353P2

(12) United States Plant Patent
Chandra et al.

(10) Patent No.: US PP34,353 P2
(45) Date of Patent: Jun. 14, 2022

(54) HYBRID BLUEGRASS NAMED 'TAES 5701'

(50) Latin Name: ***Poa arachnifera* Torr. x *P. pratensis* L.$F_1$ hybrid**
Varietal Denomination: TAES 5701

(71) Applicant: The Texas A&M University System, College Station, TX (US)

(72) Inventors: Ambika Chandra, McKinney, TX (US); James Read, Medina, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/242,515

(22) Filed: Apr. 28, 2021

(51) Int. Cl.
*A01H 5/12* (2018.01)
*A01H 6/46* (2018.01)

(52) U.S. Cl.
USPC ..... Plt./393

(58) Field of Classification Search
USPC ..... Plt./384, 393
See application file for complete search history.

(56) References Cited

U.S. PATENT DOCUMENTS

PP18,439 P2 1/2008 Hardison et al.
PP18,467 P2 1/2008 Hardison et al.

OTHER PUBLICATIONS

Meeks, M.B. 2015. Development and characterization of texas bluegrass × kentucky bluegrass interspecific hybrids for the southern United States. A Ph.D. dissertation submitted to the Office of Graduate and Professional Studies of the Texas A&M University. (Year: 2015).*

U.S. Appl. No. 17/242,507, filed Apr. 28, 2021, Chandra et al.

Meeks et al., "The application of flow cytometry and a thioredoxin-like nuclear gene for breeding *Poa arachnifera* × *Poa pratensis* hybrids." Plant Breeding, 2015, 134(5), pp. 612-622.

Meeks et al., "Growth Responses of Hybrid Bluegrass and Tall Fescue as Influenced by Light Intensity and Trinexapac-ethyl." HortScience, 2015, 50(8), pp. 1241-1247.

Kentucky Bluegrass 'Reveille', PVP Certificate No. 9800337, issued Jul. 23, 2004.

M. Meeks et al., "Registration of DALBG 1201 Hybrid Bluegrass," Journal of Plant Registrations, 2015, 9(2), 138-143.

Kentucky Bluegrass 'Limousine', PVP Certificate No. 8900052, issued Apr. 30, 1992.

* cited by examiner

*Primary Examiner* — Karen M Redden
(74) *Attorney, Agent, or Firm* — Dentons US LLP

(57) ABSTRACT

'TAES 5701' is an $F_1$ hybrid bluegrass with exceptional turfgrass quality, establishment rate, seasonal color, shoot density, fine leaf texture, and ability to persist under a range of environmental stresses typically encountered in the southern United States.

10 Drawing Sheets

Latin name of the genus and species of the plant claimed: *Poa arachnifera* Torr. x *P. pratensis* L. $F_1$ hybrid.

Variety denomination: 'TAES 5701'.

BACKGROUND OF THE INVENTION

The *Poa* genus includes approximately 200 to 300 species, both annual and perennial types, that are native to temperate regions of northern and southern hemispheres. Of these, Kentucky bluegrass (*Poa pratensis* L.) is the predominant perennial species of *Poa* used in the United States for turf and forage applications. Although it displays excellent turfgrass quality, its use in southern climates is limited because of its sensitivity to heat and drought stress. Texas bluegrass is well known for its heat and drought tolerance and is native to the southern region of the United States spanning from New Mexico to South Carolina. The first successful attempt to genetically improve stress tolerance in Kentucky bluegrass was made in 1908 by George Oliver (Vinall and Hein, 1937) by hybridizing Kentucky bluegrass with Texas bluegrass (*P. arachnifera* Torr.); however, it was not until 1998, 90 years later, that the first commercially available interspecific hybrid between Texas bluegrass and Kentucky bluegrass, 'Reveille', was developed (Read et al., 1999; PVP Certificate No. 9800337; not patented). This large span of time can be attributed to the limited amount of knowledge available for the two species as it pertains to their morphological and agronomic characteristics, as well as the complexity of their genetic compositions.

Members of the genus *Poa* exhibit different ploidy levels, diploid, polyploid, or aneuploid, with a basic chromosome number of x=7. There is great variation in chromosome number both within and among species of *Poa* (Patterson et al., 2005). Kentucky bluegrass is documented to have chromosome numbers ranging from 2n=24 to 124 (Love and Love, 1975), and Texas bluegrass chromosome numbers range from 2x=42 to 91 (Hartung, 1946; Kindiger et al., 2011).

Even though greater success in hybridization may be achieved when high polyploid parents such as Kentucky bluegrass are used as pollinators (Pepin and Funk, 1974), extreme differences in ploidy levels is still one of the greatest barriers to successful interspecific hybridization in *Poa* (Kelley et al., 2009).

Kentucky bluegrass primarily produces seed asexually through apomixis, although it does produce sexual seed at a low frequency (Grazi et al., 1961; Han, 1969, Wieners et al., 2006), and is referred to as a facultative apomict. 'Reveille' has been shown to produce 90% of its seed apomictically (Read et al., 1999). In contrast to Kentucky bluegrass, Texas bluegrass is a sexually obligate dioecious species with separate female and male plants present in the breeding population. Since the release of 'Reveille', other hybrid bluegrass cultivars with specific improvements in heat and drought tolerance, and disease resistance, have been developed, including 'Bandera' (Smith et al., 2008; not patented) and 'Thermal Blue' (also known as 'HB129'; U.S. Plant Pat. No. 18,467).

SUMMARY OF THE INVENTION

The present disclosure relates to a new and distinct interspecific *Poa arachnifera* Torr. x *P. pratensis* L. $F_1$ hybrid variety named 'TAES 5701'. 'TAES 5701', formerly tested as 00-119-18, was produced in 2000 near Dallas, Tex. by fan-mediated bag crossing between Texas bluegrass TXB 3-86 (not patented) as the female parent and Kentucky bluegrass 'Limousine' (PVP Certificate No. 8900052; not patented) as the male parent (pollen). 'TAES 5701' was first asexually propagated in Dallas, Tex. by propagating vegetative material into smaller plugs and allowing the plugs to grow before splitting them again.

'TAES 5701' is an experimental Texas bluegrass x Kentucky bluegrass interspecific hybrids developed at the Texas A&M AgriLife Research and Extension Center in Dallas, Tex., which was evaluated over a 3-year period (2010-2012) alongside 46 other experimental Texas bluegrass x Kentucky bluegrass interspecific hybrids and three commercial check varieties, including hybrid bluegrass checks ('Reveille', 'Thermal Blue Blaze' (not patented)) and 'Rebel Exeda' (not patented) tall fescue. The evaluations took place in multiple locations with test sites located in Auburn, Ala.; Dallas, Tex.; Starkville, Miss.; Raleigh, N.C.; and Knoxville, Tenn.

'TAES 5701' performed consistently well at each test location across multiple traits, including establishment rate, turfgrass quality, seasonal color, shoot density and leaf texture. 'TAES 5701' exhibited a turfgrass performance index (TPI) of 12 as compared to 'Rebel Exeda' tall fescue (with a TPI of 15), and two hybrid bluegrasses, 'Reveille' (TPI of 7), and 'Thermal Blue Blaze' (TPI of 6). Leaf texture of 'TAES 5701' is finer than 'Rebel Exeda' tall fescue and similar to hybrid bluegrass checks 'Reveille' and 'Thermal Blue Blaze'. Its superior performance over a wide range of southern test locations suggests that 'TAES 5701', a cool-season turf-type hybrid bluegrass, is well suited for use on lawns, landscape and other recreational sites across the southern United States. 'TAES 5701' is genetically stable and uniform $F_1$ hybrid bluegrass variety. Tests to determine the seed yield potential and the level of apomixis has revealed 'TAES 5701' to exhibit very low levels of fertility. 'TAES 5701' differs from its parents and all other known *Poa arachnifera* Torr. x *P. pratensis* L. $F_1$ hybrid cultivars.

The following are the most outstanding and distinguishing characteristics of 'TAES 5701': It exhibits a combination of (1) fine leaf texture, (2) lower frost injury as compared to other hybrid bluegrasses, (3) superior long-term persistence and summer performance as compared to other hybrid bluegrasses, (4) capable of asexually propagated only as sod, (5) limited anthocyanin production in culm nodes and florets, and (6) the ability to persist under a range of environmental stresses typically encountered in the southern United States.

'TAES 5701' turf can be distinguished from Texas bluegrass TXB 3-86 (female parent) at least based upon their canopy, color, and shoot density. Specifically, 'TAES 5701' exhibits a dwarf canopy, darker green color, and higher shoot density as compared to its female parent TXB 3-86. 'TAES 5701' turf can be distinguished from Kentucky bluegrass 'Limousine' (PVP Certificate No. 8900052) (male parent) at least based upon their floret characteristics. Specifically, 'TAES 5701' exhibits very low levels of fertility with poorly developed male and female reproductive organs within florets, whereas 'Limousine' is apomictic with perfect flower.

BRIEF DESCRIPTION OF THE DRAWINGS

'TAES 5701' is illustrated by the accompanying photographs, which show the turf's leaf texture and establishment as well as the claimed plants vegetative and floral characteristics. The colors shown are as true as can be reasonably obtained by conventional photographic procedures.

DETAILED BOTANICAL DESCRIPTION

Figure 1:
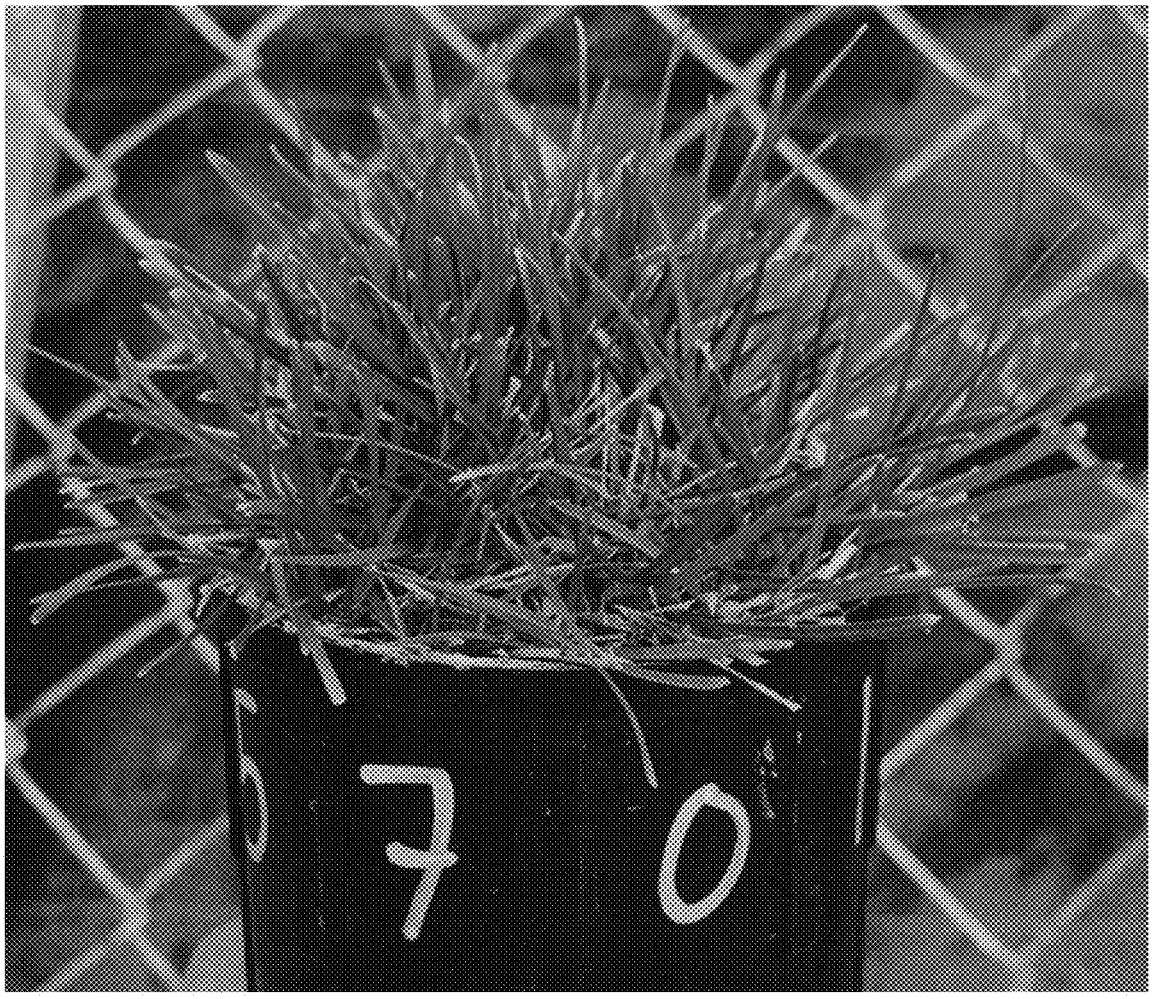
FIG. 1—Shows the fine leaf texture of 'TAES 5701'

The following detailed description sets forth the distinctive characteristics of 'TAES 5701'. The claimed plant was four months old when the data was collected in Dallas, Tex. Color references are to the Munsell Color Chart; 1977 Edition of the Munsell Color Charts for Plant Tissues, unless otherwise indicated. Color designations provided refer to both mature and immature stages unless otherwise indicated. If any Munsell color designations below differ from the accompanying photographs, the Munsell color designations are accurate.

Plant:

*Growth habit*.—Intermediate.

*Natural plant height* (*at maturity*).—12.5 cm; compact.

*Tillers on the culm*.—None.

*Self-fertility*.—Very low levels.

Rhizomes:

1st *internode length*.—9.02 mm.

2nd *internode length*.—14.66 mm.

3rd *internode length*.—15.75 mm.

4th *internode length*.—15.21 mm.

4th *internode diameter*.—0.45 mm.

4th *node diameter*.—0.93 mm.

Leaves:

*Length* (*flag leaf*).—2.5 cm.

*Width* (*flag leaf*).—2.75 mm.

*Leaf curling*.—Mild.

*Leaf sheath pubescence*.—Absent.

*Leaf sheath hairs on surface*.—Absent.

*Leaf sheath hairs on margin*.—Absent.

*Leaf sheath margin roughness* (*to touch*).—Smooth.

*Leaf sheath surface roughness* (*to touch*).—Smooth.

*Leaf sheath hairs just beneath leaf blade* (*under collar*).—Absent.

*Leaf sheath color*.—5GY value of 4 chroma of 8.

*Leaf collar color*.—2.5GY value of 8 chroma of 4.

*Anthocyanin coloration of the basal leaf sheath*.—Absent.

*Lower surface leaf coloration*.—2.5G value of 3 chroma of 4.

*Upper surface leaf coloration*.—2.5G value of 3 chroma of 4.

*Auricles*.—Absent.

*Ligules*.—Present, membranous.

*Ligule hairs*.—Absent.

*Leaf blade venation pattern*.—Parallel.

*Leaf blade color*.—2.5G value of 3 chroma of 4.

*Leaf blade color* (*winter*).—2.5G value of 3 chroma of 4.

*Leaf blade luster* (*upper side*).—Shiny.

*Leaf blade luster* (*lower side*).—Shiny.

*Leaf blade hairs on margin*.—Absent.

*Leaf blade hairs* (*upper side*).—Absent.

*Leaf blade hairs* (*lower side*).—Absent.

*Stem color*.—5 GY value of 4 chroma of 8.

*Ascending culm internode length*.—9.5 cm.

*Culm node pubescence*.—Absent.

*Time of flowering*.—Mar. 8, 2021 in Dallas, Tex.

*Glumes*.—2.88 mm in length.

*Lemma colors*.—7.5 GY value of 7 chroma of 4.

*Palea colors*.—7.5 GY value of 7 chroma of 4.

*Ligule color*.—transparent or clear.

Inflorescence:

*Type*.—Panicle.

*Collar of the rachis*.—5GY value of 7 chroma of 8.

*Panicle length*.—12.3 cm.

*Panicle diameter*.—2.1 cm.

*Color*.—7.5GY value of 7 chroma of 6.

*Stigma length*.—Poorly developed; no accurate measurement readily obtainable.

*Stigma color*.—Poorly developed; no accurate measurement readily obtainable.

*Stigma characterization*.—Poorly developed; no accurate measurement readily obtainable.

*Peduncle length*.—4.9 cm.

*Pedicel*.—2.82 mm.

*Pedicel color*.—7.5 GY value of 6 chroma of 2.

*Awns*.—Absent.

*Culm diameter*.—0.50 mm Culm color: 2.5G value of 5 chroma of 4.

*Culm anthocyanin coloration of the nodes and internodes*.—Anthocyanin at the nodes appears infrequently with a coloration close to 2.5R with a value of 4 and chroma of 4.

*Florets per spike*.—5.3 on an average.

Environmental resistance:

*Cold* (*injury*).—Moderately Resistant.

*Heat*.—Moderately Resistant.

*Drought*.—Moderately Resistant.

*Low fertility*.—Moderately Resistant.

*Alkalinity* (*ph*>7.5).—Highly Resistant.

Disease resistance:

*Leaf rust* (*puccinia gramminis pers.*).—Moderately Resistant.

Morphological analysis of 'TAES 5701': 'TAES 5701' was morphologically compared to 'Reveille'; and 'Rebel Exeda' (Table 1 and 2). Three 8-inch azalea pots of each genotype were propagated with 10.2 cm plugs of plant material on Nov. 16, 2020. Pots were buried in a sand bed in a randomized complete block design on Dec. 11, 2020 to induce vernalization. On Feb. 24, 2021, all replicate pots were removed from the sand bed and placed in a 77° F.±5° F. greenhouse. Supplemental lighting was provided with LED lights to extend daylengths to 16 hrs. The first inflorescences began emerging on March 8th (TAES 5701), March 15th ('Reveille'), and March 22nd ('Rebel Exeda'). Four sample measurements were collected from each replicate pot for a total of 12 samples per trait. Leaf blade length (cm) and width (mm) were measured from the first fully expanded leaves before stem elongation. Plant height before stem elongation (cm) was measured from the four tallest leaves. Rhizome internode lengths (mm) and diameters (mm) were measured from those with a new shoot between the first, second, third, fourth and fifth nodes. The ascending culm internode length (cm) was measured between the nodes of the first and second leaves of the four tallest inflorescences. Culm diameter (mm) measured the thickness of ascending culm. Inflorescence length or plant height were measured at full maturity from the base of the plant to tip of the inflorescence. Flag leaf length (cm) and width (mm) were measured from the four tallest inflorescences in each pot. Peduncle length (cm) was measured between the flag leaf node and base of the inflorescence. Panicle diameter (cm) and length (cm) were measured from the four tallest inflorescences. Pedicel length (mm) was measured between the node of the second branching spikelet and base of the first floret. Glume length (mm) was measured between the base of a lower glume and tip of an upper glume. The number of florets per spikelet were counted randomly from one spikelet from each of four inflorescences. The number of inflorescences were counted for each pot and averaged.

Figure 2:
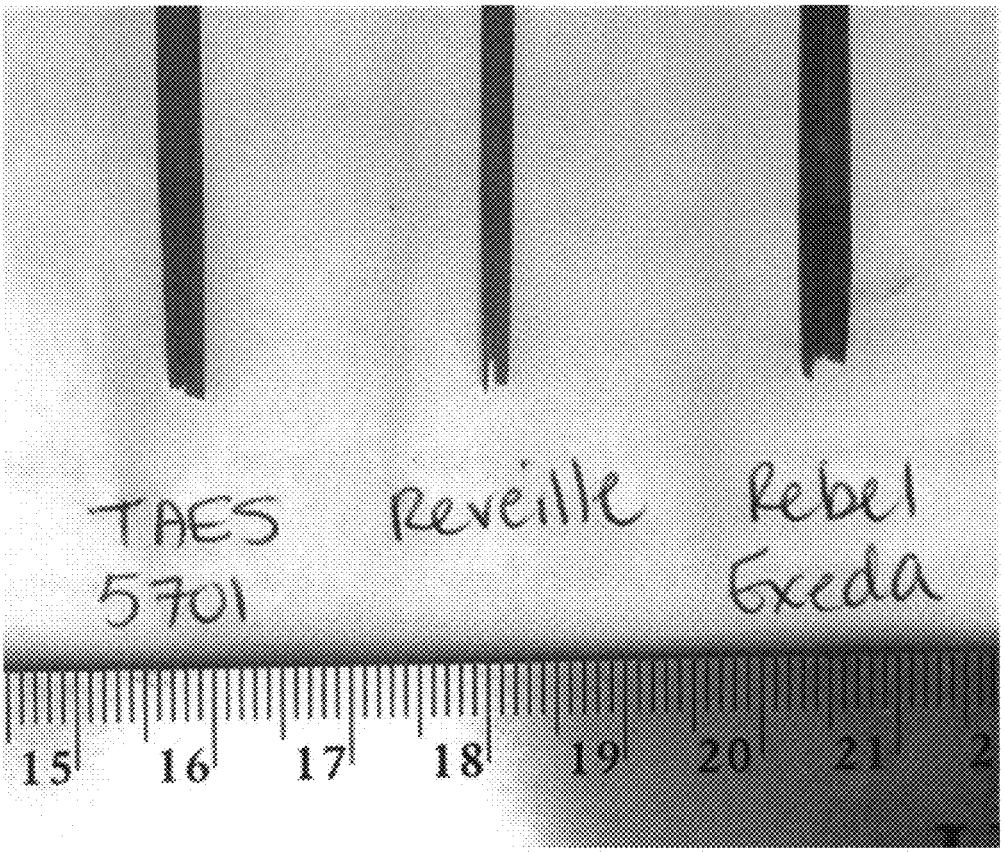
FIG. 2—Shows the leaf blade width and texture of 'TAES 5701' compared to 'Reveille' and 'Rebel Exeda'
Figure 3:
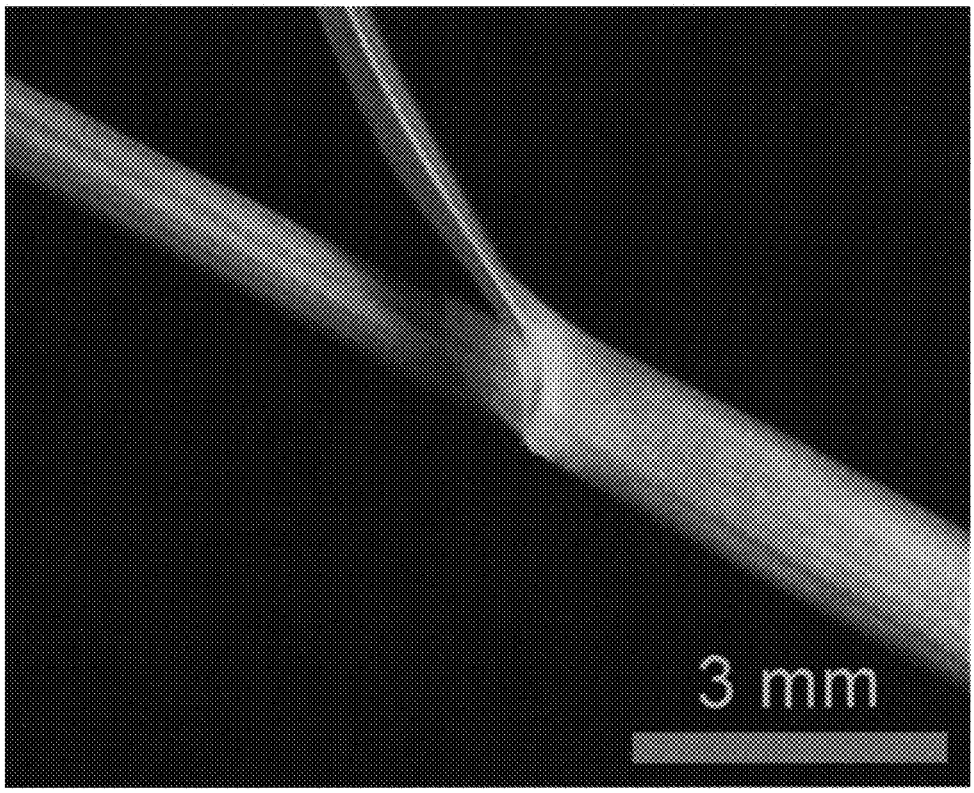
FIG. 3—Shows the membranous ligule of 'TAES 5701' at the base of each leaf and the lack auricles and ligule hairs FIG. 4—Shows an established field of 'TAES 5701' in Georgia, USA FIG. 5—Shows the absence of frost damage on 'TAES 5701' (background) as compared to 'DALBG' 1201 (U.S. application Ser. No. 17/242,507) (foreground) on Feb. 17, 2021 in Whitesburg, Ga.
Figure 4:
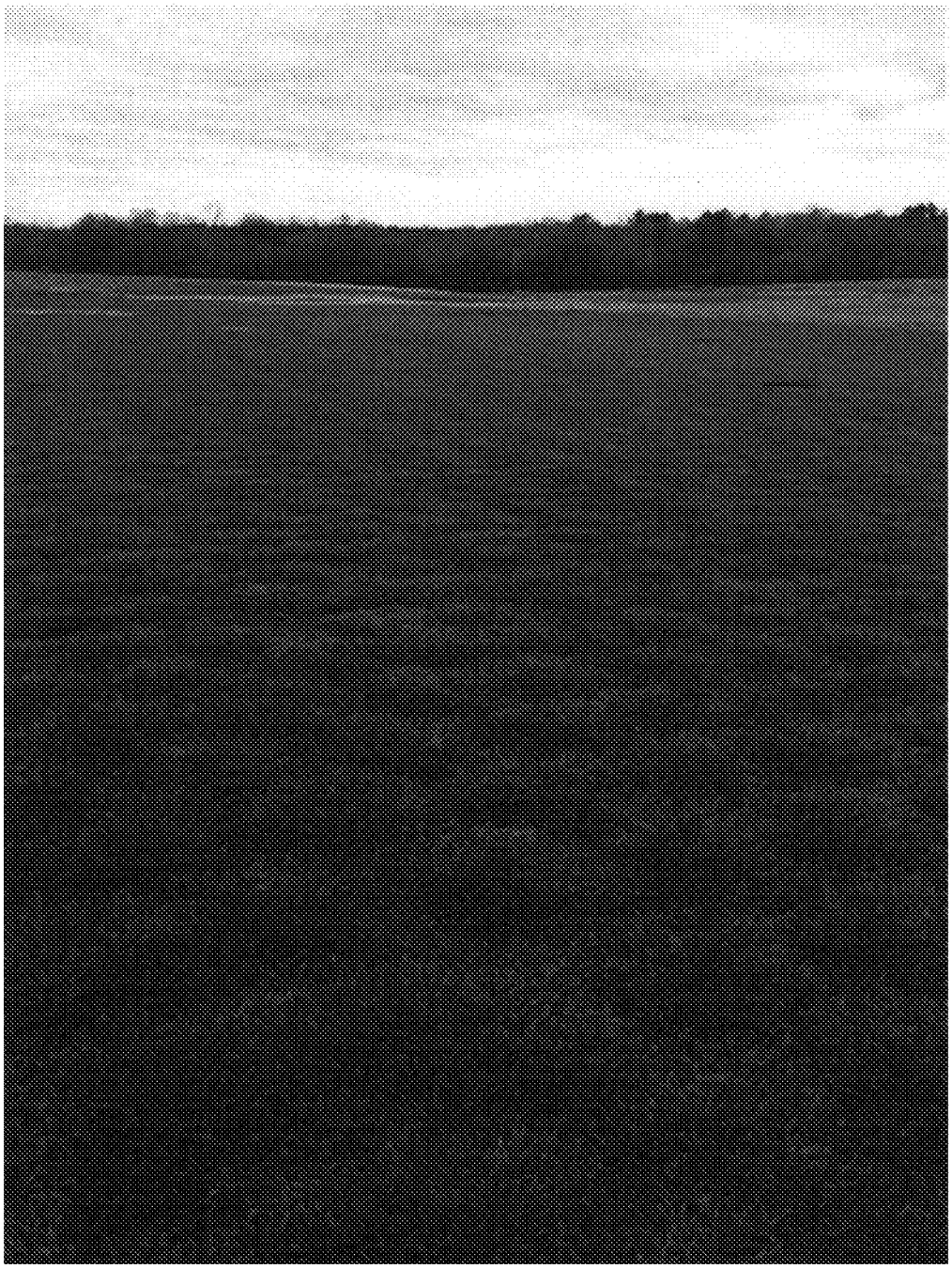
Figure 5:
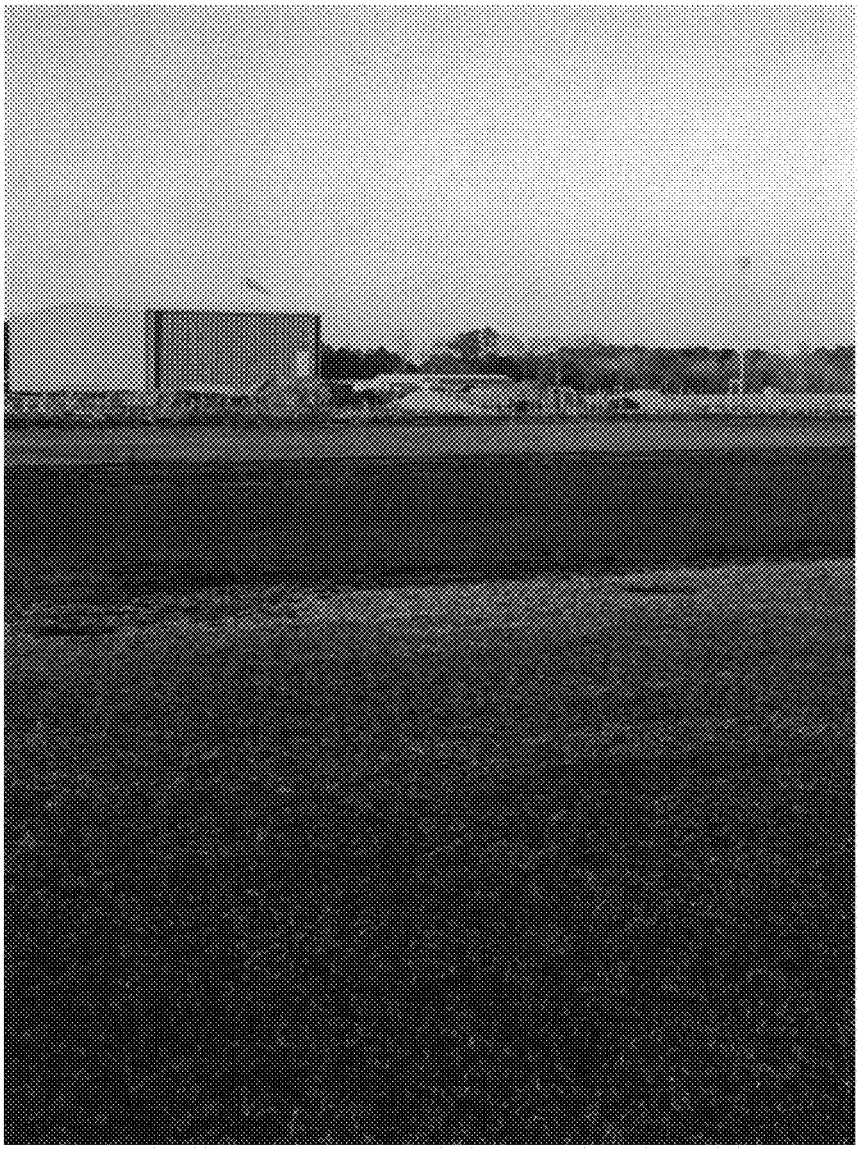

Vegetative characteristics: The leaf blade length of 'TAES 5701' is shorter than 'Reveille' and 'Rebel Exeda', but the width is narrower than 'Rebel Exeda' and wider than 'Reveille' (Table 1, FIGS. 1 and 2). 'TAES 5701' has a membranous ligule and lacks ligule hairs and auricles (FIG. 3). An established sod production field of 'TAES 5701' shows uniformity of 'TAES 5701' under large sod production (FIG. 4) and resistance to winter injury (FIG. 5). The natural plant height before stem elongation of 'TAES 5701' is more dwarf than 'Reveille' and 'Rebel Exeda' (Table 1, FIG. 6). The first and second internodes are similar between 'TAES 5701' and 'Reveille', but the third and fourth internodes are longer for 'TAES 5701' (Table 1). The fourth internode and node diameters for 'TAES 5701' are also thicker than 'Reveille' (Table 1).

Figure 6:
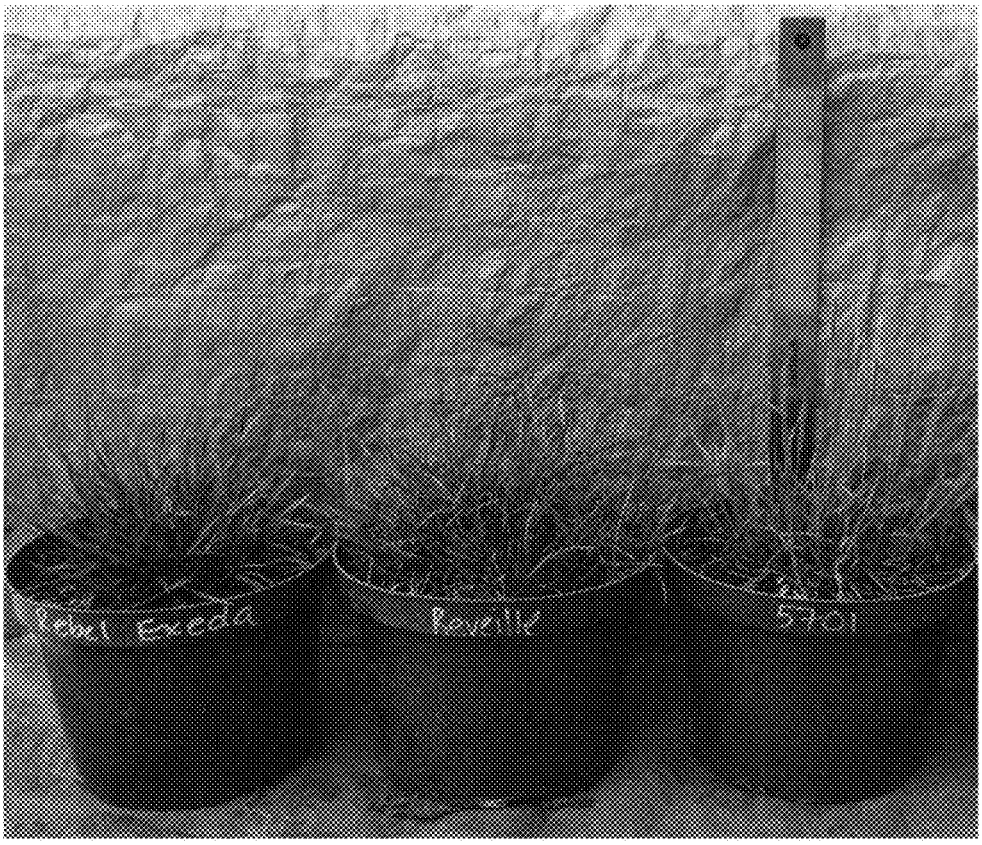
FIG. 6—Shows the natural plant height and leaf color of 'TAES 5701' compared to 'Rebel Exeda' (far left) and Reveille (middle) as photographed on Mar. 9, 2021.
Figure 7:
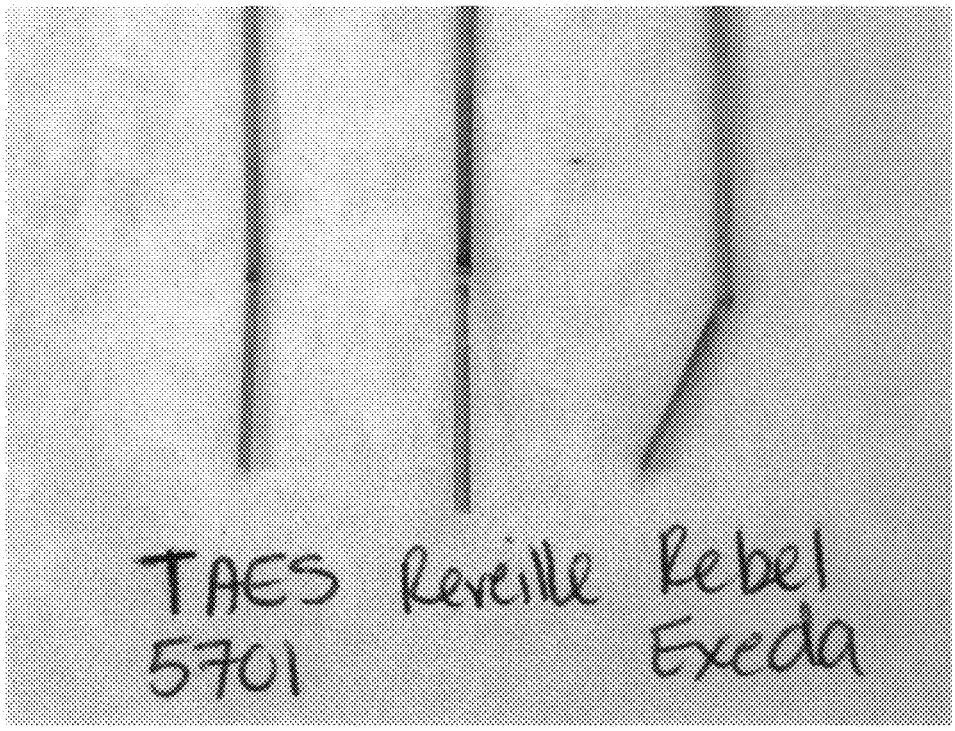
FIG. 7—Shows the ascending culm node coloration of 'TAES 5701'
Figure 8:
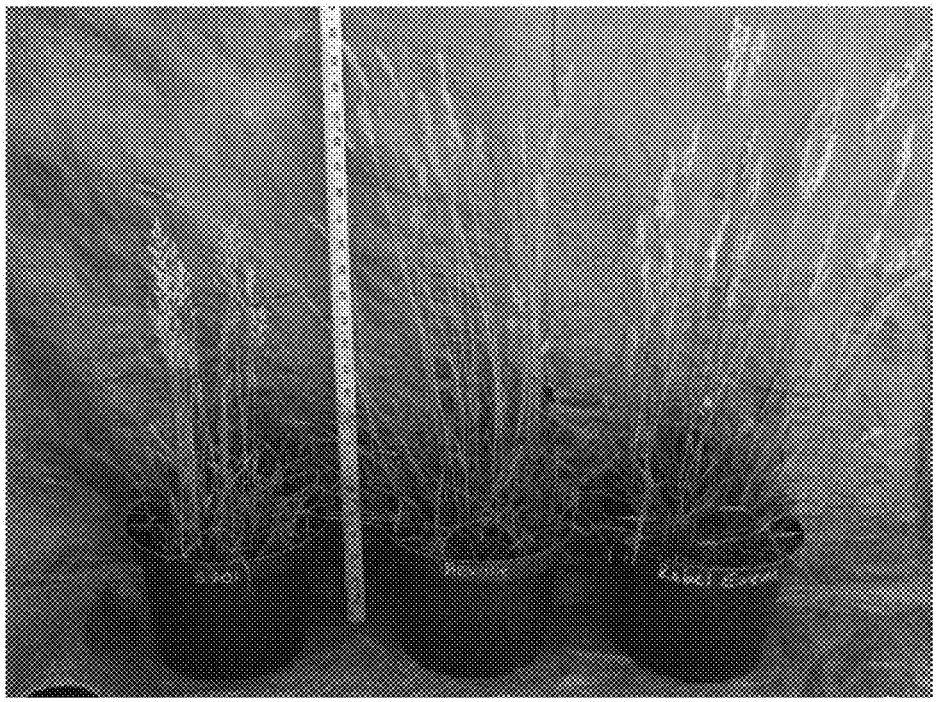
FIG. 8—Shows the mature plant height of 'TAES 5701' (left) as compared to 'Reveille' (middle) and 'Rebel Exeda' (right).
Figure 9:
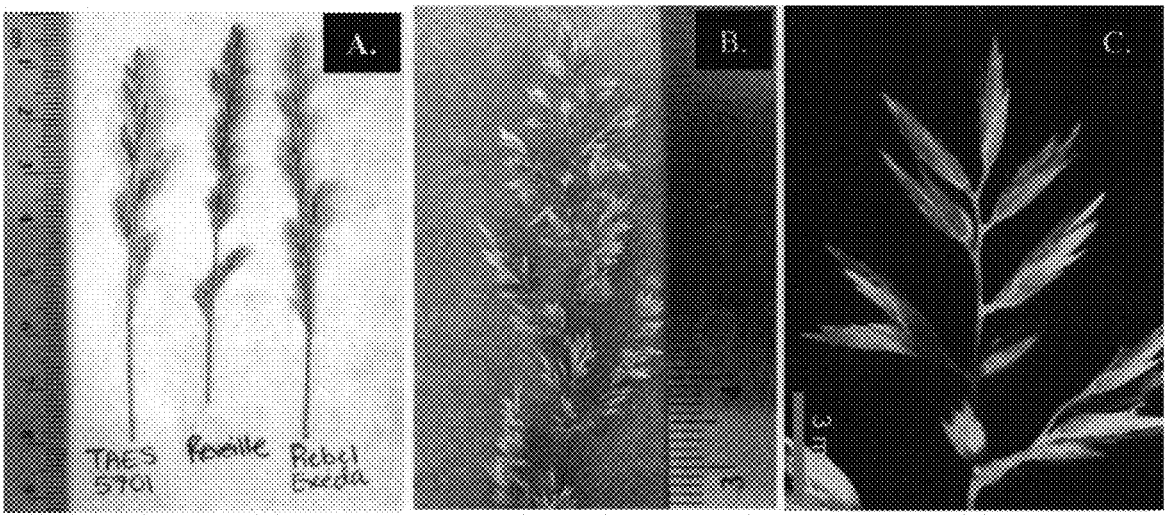
FIG. 9—Shows the panicle length of 'TAES 5701' as compared to 'Reveille' and 'Rebel Exeda' (A) as well as the anthers and well-developed stigmas at maturity (A, B, and C).
Figure 10:
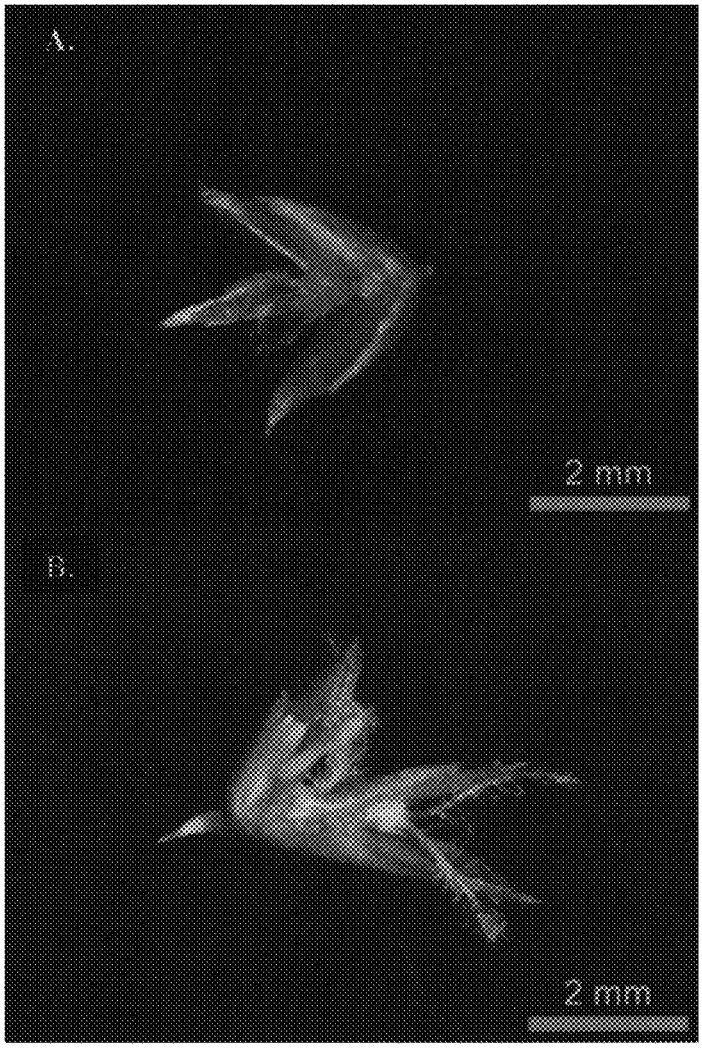
FIG. 10—Shows the dissected floret of 'TAES 5701' (A) showing stigmas exerting from the spikelet as compared to a dissected floret of 'Reveille' (B) is with anthers, stigmas, and ovary.

Floral characteristics: Stem elongation for emerging inflorescences of 'TAES 5701' began emerging on Mar. 8, 2021, one and two weeks before 'Reveille' and 'Rebel Exeda', respectively (FIG. 6). The ascending culm internode length is shorter than 'Reveille' but similar to 'Rebel Exeda', and culm diameters were not different (Table 2). However, anthocyanin is present at the culm node for 'TAES 5701' like 'Reveille', but to a much lesser degree (FIG. 7). Mature plant height including the inflorescences for 'TAES 5701' is more dwarf than 'Reveille' and 'Rebel Exeda' (Table 2, FIG. 8). Flag leaf length is similar between 'TAES 5701' and 'Reveille' but shorter than 'Rebel Exeda' (Table 2). The flag leaf width is intermediate between the two commercial cultivars, and peduncle length is much shorter (Table 2). Although no differences were observed in panicle diameter, 'TAES 5701' has a panicle length intermediate and similar to both 'Reveille' and 'Rebel Exeda' (Table 2, FIG. 9A). 'TAES 5701' produced an average of 25 inflorescences per replicate pot like 'Reveille'. Pedicle length is also intermediate for 'TAES 5701' but the number of florets per spikelet is similar (Table 2). Glume length for 'TAES 5701' is similar to 'Reveille' and shorter than 'Rebel Exeda'. Unlike 'Reveille', 'TAES 5701' does not express anthocyanin at the tips of florets at maturation or exert anthers (FIGS. 9A, B, and C). Very few stigmas have been observed and are poorly developed (FIG. 10). 'TAES 5701' exhibits very low levels of fertility which reduces the risk of off-type production to maintain genetic purity. 'TAES 5701' is only available as vegetative material (sod, sprigs and plugs) from certified sod producer(s).

TABLE 1

Statistical analysis of vegetative traits in March 2021 between 'TAES 5701', 'Reveille', and 'Rebel Exeda' tall fescue.

| | Leaf blade | | Plant height before stem | Rhizome internode length§ | |
|---|---|---|---|---|---|
| Cultivar | Length† cm | Width† mm | elongation‡ cm | 1st | 2nd mm |
| 'TAES 5701' | 5.14 c | 2.66 b | 12.54 c | 9.02 | 14.66 |
| 'Reveille' | 6.27 b | 2.10 c | 17.97 a | 12.09 | 12.39 |
| 'Rebel Exeda' | 8.49 a | 3.71 a | 16.16 b | — | — |
| Fisher's LSD¶ | 1.10 | 0.28 | 1.30 | NS | NS |
| C.V.# | 20.01 | 11.80 | 10.07 | 34.81 | 38.28 |

TABLE 1-continued

Statistical analysis of vegetative traits in March 2021 between 'TAES 5701', 'Reveille', and 'Rebel Exeda' tall fescue.

| | Rhizome | | Rhizome diameter§ | |
|---|---|---|---|---|
| | internode length§ | | 4th inter- | 4th |
| Cultivar | 3rd | 4th | node | node |
| | mm | | | |
| 'TAES 5701' | 15.75 a | 15.21 a | 0.45 a | 0.93 a |
| 'Reveille' | 10.59 b | 10.10 b | 0.33 b | 0.69 b |
| 'Rebel Exeda' | — | — | — | — |
| Fisher's LSD¶ | 3.63 | 4.31 | 0.11 | 0.15 |
| C.V.# | 32.46 | 38.57 | 31.27 | 21.85 |

†Blade leaf length (cm) and width (mm) were measured from the first fully expanded leaves before stem elongation.

‡Plant height before stem elongation (cm) was measured from the four tallest leaves.

§Rhizomes were not available for Rebel Exeda so TAES 5701 was only compared to 'Reveille'. Internode lengths and diameters were only measured from rhizomes with a new shoot.

¶Four sample measurements were collected for each replicate pot and trait for a total of 12 samples. If the ANOVA was determined to be significant at the 0.05 probability level, means were separated using Fisher's LSD.

#Coefficients of variation were calculated by dividing the root mean square error by the grand mean and multiplying by 100.

TABLE 2

Statistical analysis of floral traits in March 2021 between 'TAES 5701', 'Reveille', and 'Rebel Exeda' tall fescue.

| Cultivar | Ascending culm internode length† cm | Culm diameter‡ mm | Inflorescence length (plant height)§ cm | Flag leaf length¶ cm |
|---|---|---|---|---|
| 'TAES 5701' | 9.51 b | 0.50 | 34.03 c | 2.45 b |
| 'Reveille' | 11.75 a | 0.53 | 40.64 b | 2.88 b |
| 'Rebel Exeda' | 10.76 ab | 0.84 | 46.93 a | 4.47 a |
| Fisher's LSD## | 1.68 | NS | 2.91 | 0.70 |
| C.V. ††† | 18.92 | 64.52 | 8.64 | 25.93 |

| Cultivar | Flag leaf width¶ mm | Peduncle length# cm | Panicle diameter†† cm | Panicle length†† cm |
|---|---|---|---|---|
| 'TAES 5701' | 2.75 b | 4.88 b | 2.09 | 6.39 ab |
| 'Reveille' | 2.13 c | 11.78 a | 1.83 | 5.33 b |
| 'Rebel Exeda' | 3.55 a | 12.85 a | 1.75 | 7.37 a |
| Fisher's LSD## | 0.32 | 1.73 | NS | 1.23 |
| C.V. ††† | 14.06 | 21.10 | 16.78 | 23.32 |

| Cultivar | Pedicel length‡‡ mm | Florets per spike§§ no. | Glume length¶¶ mm |
|---|---|---|---|
| 'TAES 5701' | 2.82 c | 5.25 | 2.88 b |
| 'Reveille' | 4.08 b | 4.75 | 3.32 b |

TABLE 2-continued

Statistical analysis of floral traits in March 2021 between 'TAES 5701', 'Reveille', and 'Rebel Exeda' tall fescue.

| | | | |
|---|---|---|---|
| 'Rebel Exeda' | 5.22 a | 4.17 | 5.81 a |
| Fisher's LSD## | 0.59 | NS | 0.59 |
| C.V. ††† | 17.69 | 25.80 | 17.67 |

†The ascending culm internode length (cm) was measured between the nodes of the first and second leaves of the four tallest inflorescences.
‡Culm diameter (mm) measured the thickness of ascending culm.
§Inflorescence length or plant height were measured at full maturity from the base of the plant to tip of the inflorescence.
¶Flag leaf length (cm) and width (mm) were measured from the four tallest inflorescences in each pot.
#Peduncle length (cm) was measured between the flag leaf node and base of the inflorescence.
††Panicle diameter (cm) and length (cm) were measured from the four tallest inflorescences.
‡‡Pedicel length (mm) was measured between the node of the second branching spikelet and base of the first floret.
§§The number of florets per spikelet were counted randomly from one spikelet from each of four inflorescences.
¶¶Glume length (mm) was measured between the base of a lower glume and tip of an upper glume.
Four sample measurements were collected for each replicate pot and trait for a total of 12 samples. If the ANOVA was determined to be significant at the 0.05 probability level, means were separated using Fisher's LSD.
†††Coefficients of variation were calculated by dividing the root mean square error by the grand mean and multiplying by 100.

Establishment and turfgrass performance evaluation: 47 experimental hybrids including 'TAES 5701', along with three commercial check varieties, including hybrid bluegrass checks ('Reveille', 'Thermal Blue Blaze'); and 'Rebel Exeda' tall fescue. In 2009, all experimental hybrids and three commercial checks including, 'Rebel Exeda' tall fescue (*Festuca arundinacea* Schreb.) and two hybrid bluegrass varieties 'Reveille' and 'Thermal Blue Blaze', were planted at five locations (Auburn, Ala.; Dallas, Tex.; Knoxville, Tenn.; Raleigh, N.C. and Starkville, Miss.) in a randomized complete block design with three replications. Irrigation was applied to supplement rainfall and promote establishment in the first year and only to prevent dormancy and stress in sequential years. Plots were mowed at a height between 5.1 and 6.4 cm. Nitrogen (N) was applied in split doses across growing seasons at an annual rate of 19.53 to 29.29 g $m^2$. No pesticides were applied to prevent or control insects or diseases. Primary traits evaluated from 2010 to 2012 were summer turfgrass quality, overall turfgrass quality (spring, summer, and fall combined), seasonal color, leaf texture, and shoot density. Evidence of disease resistance were of secondary interest. All traits were evaluated on a 1 to 9 scale according to NTEP (National Turfgrass Evaluation Program), where 5=minimum acceptable and 9=excellent quality, dark green color, very fine texture, and high density. Data were analyzed using JMP Pro v.10 (SAS Inc., Cary, N.C.) using the generalized linear model for each location independently and combined. Data for 'TAES 5701' and commercial checks were analyzed separately, and means were separated using Fisher's protected LSD at the 0.05 probability level.

Traits and characteristics of 'TAES 5701': Tables 3-7 summarize the primary traits (summer turfgrass quality, overall turfgrass quality (spring, summer, and fall combined), seasonal color, leaf texture, and shoot density) evaluated from 2010 to 2012 for 'TAES 5701' and the three commercial check varieties. In addition to these evaluations, 'TAES 5701' demonstrates better tolerance to frost injury, reduced disease incidence in sod fields, and better long-term persistence and summer performance as compared to the commercial check varieties.

*Turf quality*.—No significant differences were observed among genotypes in MS or TN. The mean turfgrass quality of 'TAES 5701' was similar to 'Reveille' in AL, NC, and TX (Table 3). 'Rebel Exeda' was inferior to 'TAES 5701' in TX, but superior in AL and NC. 'Thermal Blue Blaze' was also inferior to 'TAES 5701' in NC and TX, but superior in AL. 'TAES 5701' had a mean quality rating >5.0 in each location, with an average of 5.9 across locations which was not significantly different from commercial checks. In AL, mean summer turfgrass quality of 'TAES 5701' was statistically lower than all three checks (Table 4). However, in TX, the mean summer turfgrass quality of 'TAES 5701' was statistically similar to 'Reveille' and greater than 'Thermal Blue Blaze' and 'Rebel Exeda' tall fescue. In NC, all hybrid bluegrasses were statistically similar to each other but significantly lower than 'Rebel Exeda' tall fescue. Means were not different in MS, TN, or across all five locations. The overall mean summer quality for 'TAES 5701' was 5.3 which is greater than the minimum acceptable rating of 5.0.

*Seasonal color*.—Mean seasonal color for 'TAES 5701' was similar to 'Thermal Blue Blaze' in AL, which was less than 'Reveille' and 'Rebel Exeda' tall fescue (Table 5). All three hybrid bluegrasses had similar color ratings in NC and TN, but lighter green ratings as compared to 'Rebel Exeda' tall fescue. No differences were observed between all four genotypes in MS or TX. Across locations and years, 'Rebel Exeda' had the highest overall color ratings whereas, all three hybrid bluegrasses exhibited similar genetic color with means ≥6.1.

*Shoot density*.—Although the mean shoot density of 'TAES 5701' was greater than all three checks in AL and TX, differences were not significant (Table 6). In MS, mean density for 'TAES 5701' was greater than acceptable (5.0), but was significantly less than commercial checks. The mean shoot density of 'TAES 5701' was similar to 'Reveille' and 'Thermal Blue Blaze' in NC, which was statistically less than 'Rebel Exeda' tall fescue. Overall across years and locations, the mean shoot density for 'TAES 5701' was 6.0 which was not statistically different from any of the three checks.

*Leaf texture*.—In AL, all three hybrid bluegrasses were statistically similar to each other, but finer in texture than 'Rebel Exeda' tall fescue with ratings 6.0 (Table 7). In MS, 'TAES 5701' had the finest leaf texture with a rating of 6.5 which was statistically similar to 'Thermal Blue Blaze' but finer than 'Reveille' and 'Rebel Exeda' tall fescue. Visual scores for leaf texture were not different in either NC or TN. In TX, 'TAES 5701' was visually finer in texture than 'Rebel Exeda' tall fescue and 'Thermal Blue Blaze', but similar in texture to 'Reveille'. Overall, across years and locations, mean leaf texture for 'TAES 5701' (FIG. 1) was 6.8 which was similar to both bluegrass checks but finer than the tall fescue check.

*Disease susceptibility*.—Mean percent disease ratings for rust (*Puccinia graminis* Pers.) infection were collected in AL (2010 and 2011) and NC (2012). The data showed no significant differences between 'TAES 5701' and the commercial checks with mean disease ratings ≤11% (data not shown).

TABLE 3

Mean turfgrass quality for 'TAES 5701' and three commercial checks across five test locations.

| | 1-9 | | | | | |
|---|---|---|---|---|---|---|
| Entry | Auburn, AL | Starkville, MS | Raleigh, NC | Knoxville, TN | Dallas, TX | Avg.‡ |
| 'TAES 5701' | 5.2c | 5.2 | 5.7b | 7.9 | 5.3a | 5.9 |
| 'Rebel Exeda'‡ | 6.7a | 5.4 | 6.8a | 8.0 | 4.2bc | 6.2 |
| 'Reveille'‡ | 5.7bc | 5.1 | 5.2bc | 7.9 | 4.5ab | 5.7 |
| 'Thermal Blue Blaze'‡ | 6.0ab | 4.6 | 4.9c | 8.1 | 3.4c | 5.4 |
| LSD § | 0.8 | NS | 0.6 | NS | 0.9 | NS |

†Turfgrass quality ratings were on a 1-9 scale; 1 = poor, 9 = ideal, 5 was the minimum acceptable. Mean represents turfgrass quality data for years 2010, 2011, and 2012 at each location.

‡Commercial checks 'Rebel Exeda' tall fescue and hybrid bluegrasses 'Reveille' and 'Thermal Blue Blaze'.

§Fisher's LSD values were calculated at a probability level of 0.05; NS = not significant.

TABLE 4

Mean summer turfgrass quality ratings for 'TAES 5701' and three commercial checks for five test locations

| | 1-9 | | | | | |
|---|---|---|---|---|---|---|
| Entry | Auburn, AL | Starkville, MS | Raleigh, NC | Knoxville, TN | Dallas, TX | Avg.‡ |
| 'TAES 5701' | 4.9b | 5.1 | 5.0b | 7.4 | 4.9a | 5.3 |
| 'Rebel Exeda'‡ | 6.4a | 5.0 | 7.1a | 7.7 | 3.4h | 5.9 |
| 'Reveille'‡ | 5.7a | 4.7 | 5.1b | 8.1 | 4.2ab | 5.4 |
| 'Thermal Blue Blaze'‡ | 6.1a | 4.3 | 5.1b | 8.0 | 3.6b | 5.3 |
| LSD§ | 0.8 | NS | 0.8 | NS | 1.0 | NS |

†Summer turfgrass quality ratings were on a 1-9 scale; 1 = poor, 9 = ideal, 5 was the minimum acceptable. Mean represented turfgrass quality data for Auburn, AL (2010, 2011, 2012), Dallas, TX (2010, 2011, 2012), Starkville, MS (2010, 2011), Raleigh, NC (2010, 2011, 2012), and Knoxville, TN (2010, 2011) from the months of June through September. Auburn, AL data from 2010 and 2012 only included the months of June through August.. Dallas, TX data from 2011) only included the months of August and September.
‡Commercial checks 'Rebell Exeda' tall fescue and hybrid bluegrasses 'Reveille' and 'Thermal Blue Blaze'.
§Fisher's LSD values were calculated at a probability level of 0.05; NS = Not significant.

TABLE 5

Mean seasonal color for "TAES 5701" and three commercial checks for five test locations.

| | 1-9 | | | | | |
|---|---|---|---|---|---|---|
| Entry | Auburn, AL | Starkville, MS | Raleigh, NC | Knoxville, TN | Dallas, TX | Avg.‡ |
| 'TAES 5701' | 5.2c | 5.8 | 6.2b | 6.5b | 6.3 | 6.1b |
| 'Rebel Exeda'§ | 7.2a | 6.8 | 7.4a | 7.3a | 7.0 | 7.2a |
| 'Reveille'§ | 6.4ab | 6.0 | 6.2b | 6.7b | 6.1 | 6.3b |

TABLE 5-continued

Mean seasonal color for "TAES 5701" and three commercial checks for five test locations.

| | 1-9 | | | | | |
|---|---|---|---|---|---|---|
| Entry | Auburn, AL | Starkville, MS | Raleigh, NC | Knoxville, TN | Dallas, TX | Avg.‡ |
| 'Thermal Blue Blaze'§ | 6.1bc | 6.0 | 6.0b | 6.8b | 5.9 | 6.2b |
| LSD¶ | 0.9 | NS | 0.6 | 0.5 | NS | 0.8 |

†Seasonal color was taken on a scale of 1-9; 1 = straw brown, 9 = dark green. Mean represented color data from 2010 to 2012 at each location. Starkville. MS data was presented for 2010 and 2011.
§Commercial checks 'Rebel Exeda' tall fescue, and hybrid bluegrasses 'Reveille' and 'Thermal Blue Blaze'
¶Fisher's LSD values were calculated at a probability level of 0.05.

TABLE 6

Mean shoot density for 'TAES 5701' and three commercial checks for four test locations.

| | 1-9 | | | | |
|---|---|---|---|---|---|
| Entry | Auburn, AL | Starkville, MS | Raleigh, NC | Dallas, TX | Avg.‡ |
| 'TAES 5701' | 4.7 | 6.0b | 6.7b | 6.1 | 6.0 |
| 'Rebel Exeda'§ | 3.0 | 8.5a | 8.2a | 5.9 | 6.8 |
| 'Reveille'§ | 2.7 | 8.3a | 6.2b | 5.7 | 6.1 |
| 'Thermal Blue Blaze'§ | 2.3 | 8.5a | 5.8b | 4.6 | 5.6 |
| LSD¶ | NS | 0.3 | 0.5 | NS | NS |

‡Shoot density was taken on a scale of 1-9; 9 = maximum density. Mean represented density data from Auburn, AL (2010), Dallas, TX (2010, 2011, 2012), Starkville, MS (2010.2011), and Raleigh, NC (2011, 2012).
§Commercial checks 'Rebel Exeda tall fescue, and hybrid bluegrasses 'Reveille' and 'Thermal Blue Blaze'
¶Fisher's LSD values were calculated at a probability level of 0.05.

TABLE 7

Mean leaf texture for 'TAES 5701' and three commercial checks at five test locations.

| | 1-9 | | | | | |
|---|---|---|---|---|---|---|
| Entry | Auburn, AL | Starkville, MS | Raleigh, NC | Knoxville, TN | Dallas, TX | Avg.‡ |
| 'TAES 5701' | 6.7a | 6.5a | 7.0 | 7.7 | 6.3a | 6.8a |
| 'Rebel Exeda'‡ | 3.0b | 4.3b | 5.0 | 7.0 | 2.3c | 4.0b |
| 'Reveille'‡ | 6.0a | 5.5b | 7.0 | 8.3 | 5.7a | 6.3a |
| 'Thermal Blue Blaze'§ | 6.6a | 5.8ab | 7.0 | 8.3 | 4.0b | 6.3a |
| LSD§ | 1.2 | 0.8 | NS | NS | 0.4 | 1.3 |

†Leaf texture was taken on a scale of 1-9; 1 = coarse, 9 = fine. Means represented data from Auburn, AL (2010, 2011, 2012), Dallas, TX (2012), Starkville, MS (2010, 2011), Raleigh, NC (2012), and Knoxville, TN (2011).
‡Commercial Checks 'Rebel Exeda' tall fescue and hybrid bluegrasses 'Reveille' and 'Thermal Blue Blaze'.
§LSD values were calculated at a probability level of 0.05; NS = Not significant.

What is claimed is:

1. A new and distinct interspecific hybrid variety of bluegrass named 'TAES 5701' as shown and described herein.

* * * * *